(12) United States Patent
Chen et al.

(10) Patent No.: US 11,166,805 B2
(45) Date of Patent: Nov. 9, 2021

(54) FILTER

(71) Applicant: Lifetech Scientific (Shenzhen) Co., Ltd., Shenzhen (CN)

(72) Inventors: Zhuo Chen, Shenzhen (CN); Xiaole Jia, Shenzhen (CN); Anning Li, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 181 days.

(21) Appl. No.: 16/464,614

(22) PCT Filed: Aug. 25, 2017

(86) PCT No.: PCT/CN2017/099026
§ 371 (c)(1),
(2) Date: May 28, 2019

(87) PCT Pub. No.: WO2018/103375
PCT Pub. Date: Jun. 14, 2018

(65) Prior Publication Data
US 2021/0093434 A1  Apr. 1, 2021

(30) Foreign Application Priority Data

Dec. 6, 2016  (CN) ........................... 201611110963.2

(51) Int. Cl.
*A61F 2/01*  (2006.01)
(52) U.S. Cl.
CPC ...... *A61F 2/0108* (2020.05); *A61F 2002/016* (2013.01); *A61F 2220/0016* (2013.01); *A61F 2220/0025* (2013.01)
(58) Field of Classification Search
CPC .......... A61F 2/01; A61F 2/0108; A61F 2/013; A61F 2/014; A61F 2002/016; A61F 2002/018
See application file for complete search history.

(56) References Cited

U.S. PATENT DOCUMENTS 8,801,746 B1 * 8/2014 Kreidler .................... A61F 2/01
606/200
2003/0208227 A1  11/2003 Thomas
(Continued)

FOREIGN PATENT DOCUMENTS

CN         1711978 A     12/2005
CN       204909721 U     12/2015
(Continued)

OTHER PUBLICATIONS

International Search Report dated Apr. 12, 2017 for corresponding PCT Application No. PCT/CN2016/099026.
(Continued)

*Primary Examiner* — Katherine H Schwiker
*Assistant Examiner* — Raihan R Khandker
(74) *Attorney, Agent, or Firm* — Raymond Sun

(57) ABSTRACT

A filter (10) includes a proximal end (1), a distal end (2) and a main filter body connected between the proximal end (1) and the distal end (2). The main filter body has a first filter unit (3) and a second filter unit (4), both being conical mesh structures, as well as multiple intermediate connection posts (5) connecting the first filter unit and the second filter unit. The intermediate connection posts (5) have provided thereon support posts (6). A support post (6) includes a transition segment (61) extending from an intermediate connection post (5) to a blood vessel wall, and a support segment bent and extending from the transition segment (61), and at least partially abutting the blood vessel wall. The support segment has a main body (62) bent and extending from the end of the transition segment (61) and a flexible segment (63) bent and
(Continued)

extending from the main body (62). A diameter of at least a portion of the flexible section (63) along a length thereof is smaller than a diameter of the main body (62), thereby increasing flexibility of the support section and preventing the support section from puncturing the blood vessel wall.

11 Claims, 3 Drawing Sheets

(56) References Cited

U.S. PATENT DOCUMENTS

| | | | | |
|---|---|---|---|---|
| 2004/0087999 | A1* | 5/2004 | Bosma | A61F 2/0103 606/200 |
| 2005/0234503 | A1* | 10/2005 | Ravenscroft | A61F 2/01 606/200 |
| 2005/0267515 | A1* | 12/2005 | Oliva | A61F 2/0105 606/200 |
| 2007/0167974 | A1* | 7/2007 | Cully | A61B 17/221 606/200 |
| 2008/0275487 | A1* | 11/2008 | Fleming | A61F 2/0108 606/200 |
| 2010/0049238 | A1 | 2/2010 | Simpson et al. | |
| 2010/0121373 | A1* | 5/2010 | Tekulve | A61F 2/01 606/200 |
| 2012/0143238 | A1* | 6/2012 | Sogard | A61F 2/0105 606/200 |
| 2013/0006295 | A1 | 1/2013 | Chanduszko et al. | |

FOREIGN PATENT DOCUMENTS

| | | |
|---|---|---|
| CN | 204909721 U | 12/2015 |
| CN | 105662646 A | 6/2016 |
| CN | 105796207 A | 7/2016 |
| CN | 106308974 A | 1/2017 |
| CN | 206630733 U | 11/2017 |
| CN | 108143518 B | 10/2020 |

OTHER PUBLICATIONS

European Search Report dated Sep. 14, 2020 for corresponding European Application No. 17877963.3.
First Office Action for corresponding China Application No. 201611110962.2.
Second Office Action for corresponding China Application No. 201611110962.2.
Office Action for corresponding India Application No. 201917026442.

* cited by examiner

FILTER

FIELD

The present disclosure relates to a cardiovascular medical device, and more particularly relates to a withdrawable vena cava filter implanted into a blood vessel by means of intervention.

BACKGROUND

Pulmonary embolism (PE) is a common disease, causing a high mortality rate. According to a statistical data, the mortality rate caused by untreated pulmonary embolism is 20 to 30 percent. Every year, new cases are about 0.2 percent of the population. There are 2,700,000 new cases according to the population of 1.35 billion of China.

Various exfoliated emboli in systemic circulation may cause a pulmonary embolism. Thrombi are the most common pulmonary emboli. There are various factors in the formation of thrombosis, including slow venous blood flow and blood stasis, blood stasis, or increase of thrombocyte and blood coagulation factors, and enhancement of blood adherence which may all be caused by traumatism or bone fracture, trauma, a significant surgical procedure, extensive burn, gestation, childbirth, confinement to bed by long illnesses, sedentariness in a long-distance bus or a flight, sitting still and squatting for long periods of time, and the like. These thrombi are generally slightly adhered to a lumen wall and are prone to fall off, and dropped emboli may cause severe lesions such as a pulmonary embolism. A venous thrombus may be formed in any part, and most commonly in the lower limb.

It has been clinically proven that a vena cava filter (hereinafter referred to as "filter") is a safe and effective mechanism for preventing pulmonary embolism and may reduce the incidence rate of pulmonary embolism. However, after the filter has been implanted into an inferior vena cava for a certain time, stimulation to a blood vessel would cause a filter supporting rod be covered by the growth of endothelial cells to varying degrees, so it is difficult to remove the filter, and then the filter may only be used as a permanent filter for a long time in the human body. And the permanent filter implanted into the human body may cause certain risks. For example: the filter is in contact with blood and blood vessel endothelium for a long time, which probably leads to protein adsorption and platelet adhesion, and eventually causes thrombosis, and the thrombosis will result in venous blockage or a recurrence of pulmonary embolism; and there is a risk that the filter implanted for a long time in the human body may deform, tilt, shift, break or even penetrate the blood vessel, and the like.

At present, there are mainly two solutions in the industry to solve the problem of a filter that cannot be easily removed from the human body. One solution is to form a coating layer for preventing cell growth on the surface of the filter through a surface modification method, so as to prevent the endocardium from growing over the surface of the filter. The other solution is a method of structural design, by which the filter has two closed ends and open supporting rods abutting with the blood vessel wall to separate the filter from the blood vessel wall.

Chinese patent No. CN102330059B is a typical example of the first solution, which uses the surface modification method to deposit a polyethylene glycol-like thin film on the surface of the filter and makes use of anti-protein and cell adhesion characteristics of polyethylene glycol to inhibit the cell growth on the surface of the filter, and prevent endothelial cells from covering the supporting rods, so that the filter can be withdrawn. However, a film layer prepared by the solution may only prevent the cell growth within a period of time because of its water solubility, so that there is a stringent requirement for selection of the removal time.

For the second solution, as the filter is compressed in a sheath before being placed into the blood vessel, and after the sheath delivers the filter to a required position and releases it, the filter would expand in the blood vessel to expand the blood vessel wall. When the filter contracts or expands, the open supporting rods may be twisted with one another, which could result in a failure in expansion of the filter in the blood vessel, and reduces the usability of the filter and makes it difficult to successfully perform the surgery. Furthermore, there is a risk that the tail end of each open supporting rod punctures through the blood vessel wall, so that the incidence rate of postoperative complications is increased.

Therefore, an urgent problem to be solved involves how to guarantee reliable fixing of the vena cava filter, high efficiency of the thrombus filter, low blood vessel puncture risk, minimal endothelium growth and guaranteed withdrawal of the filter.

SUMMARY

The present disclosure provides a vena cava filter which would not puncture through a blood vessel wall or cause twisting and has a higher usability, so as to overcome the defects in the prior art.

The technical solution adopted by the present disclosure is as follows: a filter, including a proximal end, a distal end and a filter main body connected between the proximal end and the distal end. The filter main body includes a first filter unit and a second filter unit which are both of conical mesh structures, and a plurality of middle connecting rods for connecting the first filter unit with the second filter unit. A supporting rod is arranged on the middle supporting rod. The supporting rod includes a transition section extending from the middle connecting rod towards a direction away from the axis of the filter, and a supporting section bending from the transition section towards a direction close to the axis of the filter and extending towards the distal end. The supporting section includes a body bending and extending from a tail end of the transition section, and a flexible section connected with the body. The rigidity of the flexible section is less than that of the body.

In one embodiment of the present disclosure, the radial size of at least one part of the flexible section in a lengthwise direction of the flexible section is less than that of the body.

In one embodiment of the present disclosure, a cross section of the flexible section along the lengthwise direction of the flexible section has an upper contour line and a lower contour line opposite to the upper contour line in a spaced-apart manner, and the upper contour line and the lower contour line approach each other along an extension direction of the flexible section.

In one embodiment of the present disclosure, a cross section of the flexible section along the lengthwise direction of the flexible section has an upper contour line and a lower contour line opposite to the upper contour line in a spaced-apart manner, and both the upper contour line and the lower contour line are wavy lines.

In one embodiment of the present disclosure, a wave crest of the upper contour line is opposite to a wave crest of the lower contour line, and a wave trough of the upper contour line is opposite to a wave trough of the lower contour line.

In one embodiment of the present disclosure, a wave crest of the upper contour line is opposite to a wave trough of the lower contour line.

In one embodiment of the present disclosure, the radial size of the flexible section along a lengthwise direction of the flexible section is equal, and is less than the radial size of the body.

In one embodiment of the present disclosure, the flexible section is made of a flexible material.

In one embodiment of the present disclosure, an included angle between the body and the middle connecting rod is less than 90 degrees.

In one embodiment of the present disclosure, an included angle between the flexible section and the body is an obtuse angle, and the flexible section and the body are in smooth transition.

In one embodiment of the present disclosure, each supporting section further includes a protruding portion that has a smooth outer contour and is arranged at the tail end of the flexible section, and the protruding portion and the flexible section are in smooth transition.

In one embodiment of the present disclosure, supporting rods on two adjacent middle connecting rods are staggered.

The tails of the supporting rods of the filter of the present disclosure are provided with the flexible sections and the protruding portions having the smooth outer contours, and the parts of the outer contours of the protruding portions that are transitioned to the flexible sections are in smooth transition, so this structural design reduces the risk that the supporting sections puncture through a blood vessel wall, and avoids postoperative complications caused by the supporting sections puncturing through the blood vessel wall, and solves the problem of mutual twisting of the open supporting rods during contracting or expansion of the filter, and improves the availability of the filter and guarantees a surgical success.

BRIEF DESCRIPTION OF THE DRAWINGS

The present disclosure will be further described below in combination with accompanying drawings and embodiments. In the drawings.

DETAILED DESCRIPTION

To understand technical features, objectives and effects of the present disclosure more clearly, specific implementation modes of the present disclosure are described in detail now in combination with the accompanying drawings.

Figure 1:
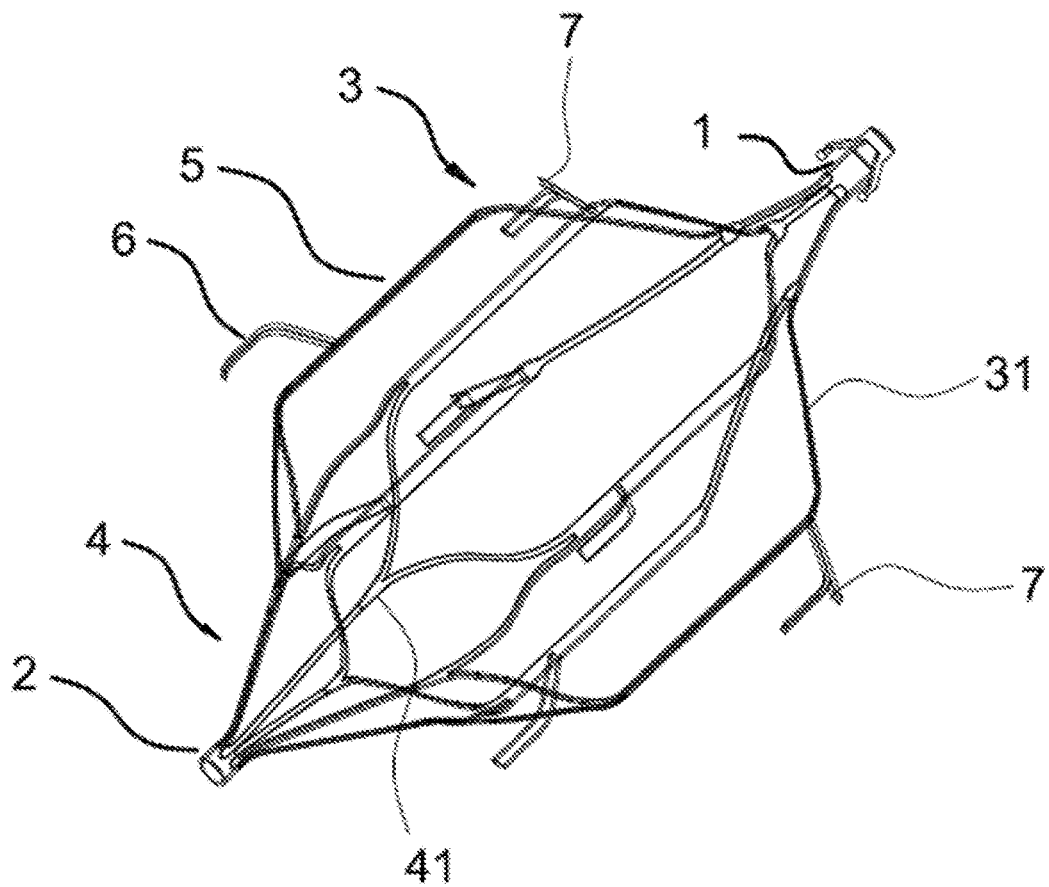
FIG. 1 is a structural schematic diagram of a filter provided by one embodiment of the present disclosure.
Figure 2:
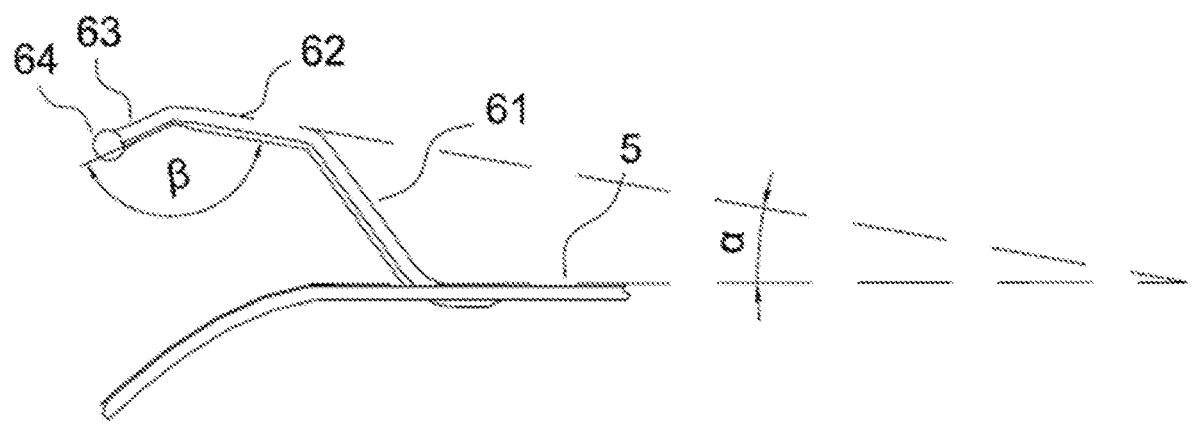
FIG. 2 is a structural schematic diagram of a supporting rod of the filter of the present disclosure.

As shown in FIG. 1 and FIG. 2, a filter 10 includes a distal end 1, a proximal end 2 and a filter main body connected between the distal end 1 and the proximal end 2. The filter main body includes a first filter unit 3, a second filter unit 4 and multiple middle connecting rods 5 for connecting the first filter unit 3 with the second filter unit 4. The multiple middle connecting rods 5 are uniformly distributed around a connecting line between the distal end 1 and the proximal end 2 in a spaced-apart manner. The first filter unit 3 is of a conical mesh structure and formed by gathering multiple Y-shaped filter mesh rods 31 at the distal end 1, and the second filter unit 4 is of a conical mesh structure and also formed by gathering multiple Y-shaped filter mesh rods 41 at the proximal end 2. Furthermore, the number of the Y-shaped filter mesh rods 31 of the first filter unit 3 is half the number of the Y-shaped filter mesh rods 41 of the second filter unit 4, so that the filter 10 is of an overall asymmetric structure. This asymmetric structure is for selective thrombi to be filtered, that is, the filter only filters the thrombi causing pulmonary embolism, so as to guarantee long-term patency of a vena cava. Meanwhile, the distal end 1 of the filter is also provided with a withdrawing hook (not marked) connected with a catcher when recycling a temporary filter.

Supporting rods 6 abutting the blood vessel wall are also arranged on the middle connecting rods 5 to enable the middle connecting rods 5 to be spaced away from the blood vessel wall, so as to prevent a problem of short recovery window caused by the adhesion of the endocardium to the surface of the filter. The supporting rods 6 include transition sections 61 extending from the middle connecting rods 5 towards a direction away from the axis of the filter 10, and supporting sections extending from the transition sections 61 towards the proximal end. At least part of the supporting sections is used for replacing the connecting rods 5 to abut with the blood vessel wall. Fixing anchors 7 for puncturing into the blood vessel wall are also arranged on some of the supporting rods 6. The fixing anchors 7 may enable the filter to be fixed more stably in the blood vessel.

Furthermore, in the present embodiment, only one supporting rod 6 is arranged on one middle connecting rod 5, and the positions of the supporting rods 6 on adjacent middle connecting rods 5 are different, and the supporting rods are arranged in a staggered manner, so that the supporting rods may provide a more uniform and stable supporting force for the filter; and it is able to prevent the thrombus filtering capability of the filter from being less effective due to inclination and displacement of the filter in the blood vessel, and the risk of postoperative pulmonary embolism may increase after surgery. In other possible embodiments, two or more supporting rods also may be arranged on each middle connecting rod. These supporting rods may be fixed at any position on the middle connecting rod as long as the direction of an opening defined by the transition sections and the supporting sections of the supporting rods are opposite to the direction in which the filter is removed.

As shown in FIG. 2, each supporting section includes a body 62 bending and extending from the tail end of each transition section 61 and abutting with the blood vessel wall, a flexible section 63 extending from the body 62 towards the proximal end, and a protruding portion 64 arranged at the tail end of the flexible section 63 and having a smooth outer contour. The protruding portion 64 and the flexible section 63, as well as the body 62 and the flexible section 63, are in smooth transition. The smooth transition mentioned in the present disclosure means that a joint of two elements is in arcuate transition or chamfering transition. The rigidity of the flexible section 63 is less than that of the body 62. There are various methods to make the rigidity of the flexible section 63 to be less than that of the body 62. In the present embodiment, the method is to make the radial size of at least part of the flexible section 63 in a lengthwise direction less than that of the body 62. Through reducing the radial size, the flexibility of this part of the supporting section may be improved, so that it is able to prevent the supporting section from puncturing through the blood vessel wall when the supporting section abuts with the blood vessel wall. The flexible section 63 also may be made of a flexible material, such as silica gel.

Further, an included angle between the body 62 and the middle connecting rod 5 is less than 90 degrees. It can be predicted that if the included angle between the body 62 and the middle connecting rod 5 is equal to 90 degrees, when the filter expands in the blood vessel, the body 62 would point to the blood vessel wall, which undoubtedly increases the risk that the supporting section would puncture through the blood vessel wall. If the included angle between the body 62 and the middle connecting rod 5 is more than 90 degrees, for example, when the body 62 and the transition section 61 are located on the same straight line, the body 62 still points to the blood vessel wall and is unable to support the blood vessel wall. In the present embodiment, the flexible section 63 and the body 62 define an obtuse angle or are located on the same straight line, but the flexible section 63 and the body 62 should not define an acute angle, and the reasons are as mentioned above.

The part of the flexible section 63 that has a radial size less than that of the body 62 may be defined by means of stripping, and the flexible section 63 may have different shapes. Specific descriptions are made below through several specific embodiments.

Embodiment I

Figure 3:
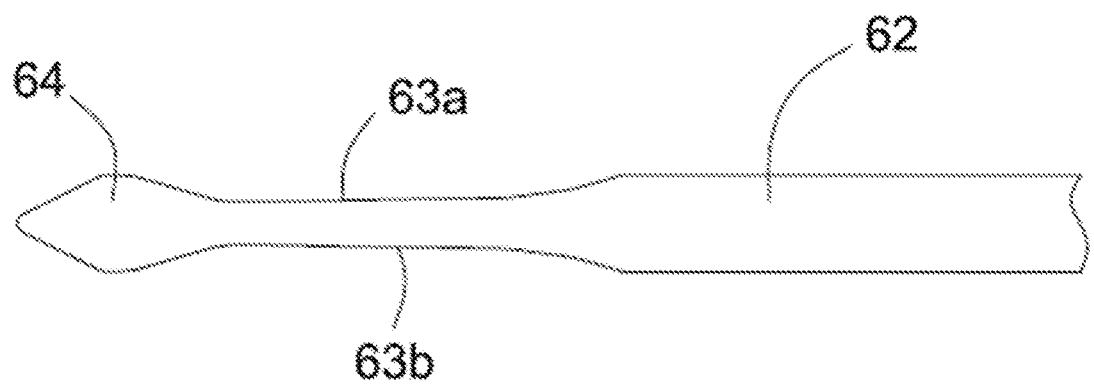
FIG. 3 is a cross sectional view of a first embodiment of a flexible section of the supporting rod of the filter of the present disclosure.

As shown in FIG. 3, the cross section of each flexible section 63 along the lengthwise direction of the flexible section 63 has an upper contour line 63a and a lower contour line 63b opposite to the upper contour line 63a in a spaced-apart manner, and the upper contour line 63a and the lower contour line 63b gradually approaches each other along an extension direction of the flexible section 63. In other words, the radial size of the flexible section 63 is gradually reduced in its extension direction. The flexible section 63 and the body 62 are in arcuate transition. The tail end of the flexible section 63 is provided with a protruding portion 64 having a quadrilateral cross-sectional shape. The four side edges of the cross section of the protruding portion 64 are all in smooth transition, and the protruding portion 64 and the flexible section 63 are also in arcuate transition. The protruding portion 64 may have a smooth outer contour provided by a mechanical method such as mechanical sand blasting and polishing, or by a chemical method or by argon arc welding. The protruding portion 64 added at the tail end of the flexible section 63 can further reduce the risk of the supporting section puncturing through the blood vessel wall.

Embodiment II

Figure 4:
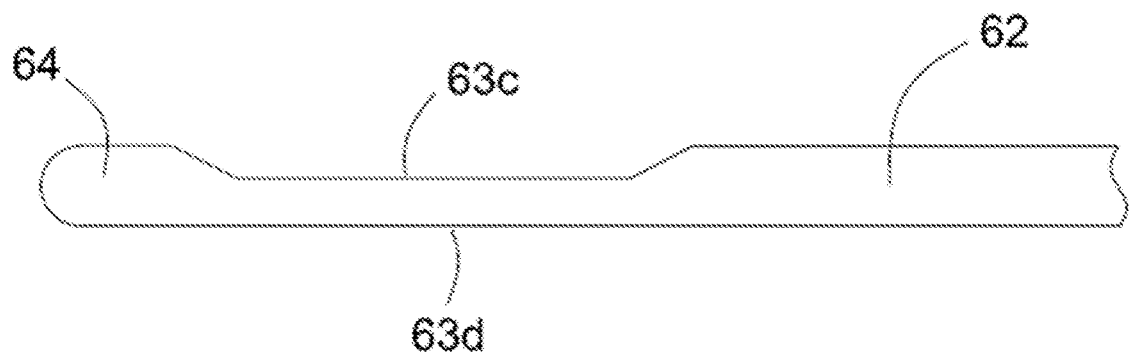
FIG. 4 is a cross sectional view of a second embodiment of a flexible section of the supporting rod of the filter of the present disclosure.

As shown in FIG. 4, the cross section of each flexible section 63 along the lengthwise direction of the flexible section 63 has an upper contour line 63c and a lower contour line 63d opposite to the upper contour line 63c in a spaced-apart manner. In the present embodiment, the lower contour line 63d and the contour line of the body 62 are located on the same straight line. The upper contour line 63c approaches the lower contour line 63d along the extension direction of the flexible section 63, and the radial size of the entire flexible section 63 is equal. In addition, the upper contour line 63c of the flexible section 63 and the outer contour of the body 62 are in chamfering transition. From the appearance, the flexible section 63 is a section having a sunken groove formed in the tail section of the supporting section by means of stripping. It can be understood that the flexible section 63 also may be two sections of grooves formed in the upper and lower sides of the tail section of the supporting section by means of stripping, and has an equal radial size along its extension direction. In the present embodiment, the cross section of the protruding portion 64 arranged at the tail end of the flexible section 63 is of an approximately shaped like a runway, and the protruding portion 64 and the upper contour line 63c of the flexible section 63 are in chamfering transition.

Embodiment III

Figure 5:
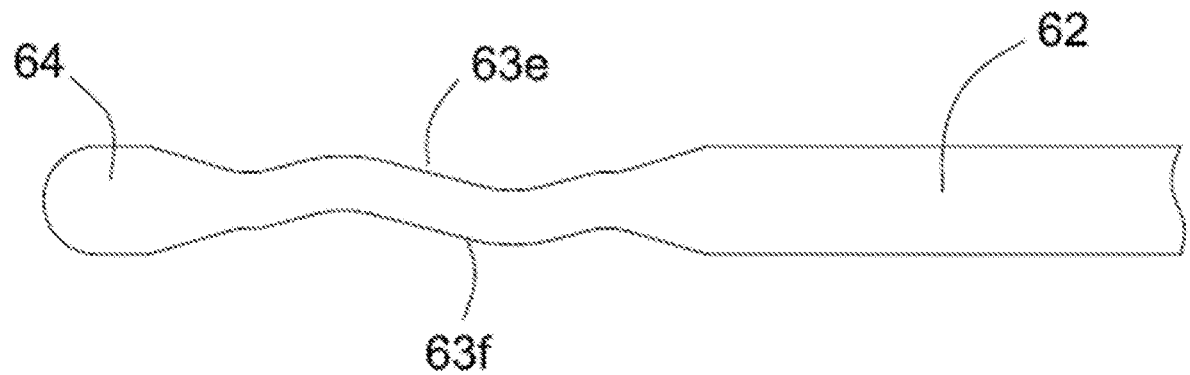
FIG. 5 is a cross sectional view of a third embodiment of a flexible section of the supporting rod of the filter of the present disclosure.

As shown in FIG. 5, the cross section of the flexible section 63 along the lengthwise direction of the flexible section 63 has an upper contour line 63e and a lower contour line 63f opposite to the upper contour line 63e in a spaced-apart manner, and the upper contour line 63e and the lower contour line 63f are both wavy lines. The wave crests of the upper contour line 63e are opposite to the wave crests of the lower contour lines 63f, and the wave troughs of the upper contour line 63e are opposite to the wave troughs of the lower contour lines 63f. In the present embodiment, the cross section of the protruding portion 64 arranged at the tail end of the flexible section 63 is of a water drop shape, and the protruding portion 64 and the flexible section 63 are in arcuate transition. The flexible section 63 and the body 62 are in arcuate transition.

Embodiment IV

Figure 6:
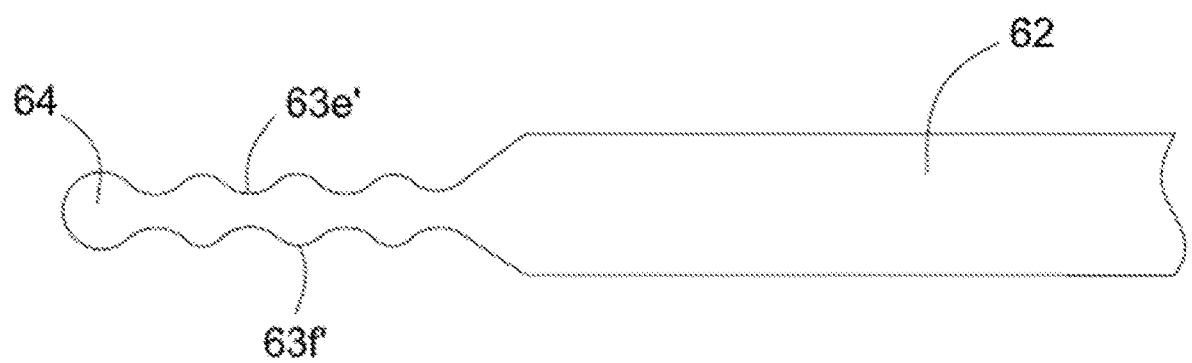
FIG. 6 is a cross sectional view of a fourth embodiment of a flexible section of the supporting rod of the filter of the present disclosure.

As shown in FIG. 6, as in the previous embodiments, the cross section of the flexible section 63 along the lengthwise direction of the flexible section 63 has an upper contour line 63e' and a lower contour line 63f' opposite to the upper contour line 63 e' in a spaced-apart manner, and the upper contour line 63e' and the lower contour line 63f are both wavy lines. But in the present embodiment, the wave crests of the upper contour line 63e' are opposite to the wave troughs of the lower contour lines 63f, and the wave troughs of the upper contour line 63e' are opposite to the wave crests of the lower contour lines 63f. In the present embodiment, the cross section of the protruding portion 64 arranged at the tail end of the flexible section 63 is circular, and the protruding portion 64 and the flexible section 63 are in arcuate transition. The flexible section 63 and the body 62 are in arcuate transition.

In all the above-mentioned embodiments, the protruding portion 64 may be of any shape. For example, the protruding portion may be elliptical as long as its outer contour is treated to be smooth to avoid the risk of puncturing through the blood vessel wall. Furthermore, when multiple supporting rods 6 are arranged on each middle connecting rod 5, the protruding portions 64 may be selectively arranged at the tail ends of the flexible sections 63.

As the tails of the supporting rods of the filter of the present disclosure are provided with the flexible sections and the protruding portions having the smooth outer contours, and the parts of the outer contours of the protruding portions that are transitioned to the flexible sections are in smooth transition, this structural design reduces the risk that the supporting sections can puncture through the blood vessel wall, and avoids postoperative complications caused the supporting sections puncturing through the blood vessel wall as much as possible, and solves the problem of mutual twisting of the open supporting rods during contracting or expansion of the filter, and improves the usability of the filter and guarantees a surgical success.

The invention claimed is:

1. A filter having an axis and comprising a proximal end, a distal end and a filter main body connected between the proximal end and the distal end, with the filter main body defining an axis and comprising:
   a first filter unit and a second filter unit which both have a conical mesh structure;
   a plurality of middle connecting rods for connecting the first filter unit with the second filter unit; and
   a plurality of supporting rods, each arranged on a separate middle connecting rod of the plurality of middle supporting rods; wherein each supporting rod comprises:
      a transition section extending from its separate middle connecting rod towards a direction away from the axis of the filter, the transition section having a tail end; and
      a supporting section bending from the transition section towards the axis of the filter and extending towards the proximal end, the supporting section comprising a body bending and extending from the tail end of the transition section, and a flexible section connected with the body, and wherein the flexible section and the body both have a rigidity, with the rigidity of the flexible section being is less than the rigidity of the body; and wherein the body and the middle connecting rod define an included angle, and the included angle is less than 90 degrees.

2. The filter of claim 1, wherein the flexible section and the body both have a radial size, with the radial size of at least one part of the flexible section in a lengthwise direction of the flexible section being less than the radial size of the body.

3. The filter of claim 2, wherein the flexible section defines a longitudinal direction and has a cross-section along the longitudinal direction which has an upper contour line and a lower contour line that is spaced-apart from and opposite to the upper contour line, and wherein the upper contour line and the lower contour line approach each other along an extension direction of the flexible section.

4. The filter of claim 2, wherein the flexible section defines a longitudinal direction and has a cross-section along the longitudinal direction which has an upper contour line and a lower contour line that is spaced-apart from and opposite to the upper contour line, and wherein both the upper contour line and the lower contour line are wavy lines.

5. The filter of claim 4, wherein the upper contour line has wave crests and wave troughs, and the lower contour line has wave crests and wave troughs, and wherein a wave crest of the upper contour line is opposite to a wave crest of the lower contour line, and a wave trough of the upper contour line is opposite to a wave trough of the lower contour line.

6. The filter of claim 4, wherein the upper contour line has wave crests, and the lower contour line has wave troughs, wherein a wave crest of the upper contour line is opposite to a wave trough of the lower contour line.

7. The filter of claim 1, wherein the flexible section and the body both have a radial size, and the flexible section defines a longitudinal direction, wherein the radial size of any point of the flexible section along the longitudinal direction of the flexible section is equal, and is less than the radial size of the body.

8. The filter of claim 1, wherein the flexible section is made of a flexible material.

9. The filter of claim 1, wherein the included angle is a first included angle, and a second included angle is defined between the flexible section and the body, the second included angle being an obtuse angle, and wherein the flexible section and the body are in smooth transition.

10. The filter of claim 1, wherein the flexible section has a tail end, and wherein the supporting section further comprises a protruding portion that has a smooth outer contour and is arranged at the tail end of the flexible section, and the protruding portion and the flexible section are in smooth transition.

11. The filter of claim 1, wherein supporting rods on two adjacent middle connecting rods are staggered.

* * * * *